United States Patent [19]

Baral

[11] Patent Number: 5,273,739

[45] Date of Patent: Dec. 28, 1993

[54] COMPOSITION AND TREATMENT FOR DARKENING HAIR COLOR

[76] Inventor: Jim Baral, 150 Central Park South, Apt. 504, New York, N.Y. 10019

[21] Appl. No.: 972,097

[22] Filed: Nov. 5, 1992

Related U.S. Application Data

[63] Continuation of Ser. No. 623,352, Dec. 7, 1990, abandoned.

[51] Int. Cl.⁵ .................................................. A61K 7/06
[52] U.S. Cl. ........................................ 424/70; 424/63; 514/554; 514/557; 514/725; 8/405
[58] Field of Search .................... 424/63, 70, 59; 514/554, 557, 725; 8/405

[56] References Cited

U.S. PATENT DOCUMENTS

| | | | |
|---|---|---|---|
| 3,729,568 | 4/1973 | Kligman | 424/318 |
| 3,906,108 | 9/1975 | Felty | 424/318 |
| 4,105,783 | 8/1978 | Yu et al. | 424/283 |
| 4,148,924 | 4/1979 | Smith et al. | 424/344 |
| 4,234,599 | 11/1980 | Van Scott et al. | 424/279 |
| 4,545,977 | 10/1985 | Gaull | 424/10 |
| 4,608,392 | 8/1986 | Jacquet et al. | 514/844 |
| 4,654,354 | 3/1987 | Shroot et al. | 514/372 |
| 4,695,452 | 9/1987 | Gannis et al. | 424/59 |
| 4,727,088 | 2/1988 | Scott et al. | 514/725 |
| 4,740,432 | 4/1988 | Bosserelle | 424/59 |
| 4,740,519 | 4/1988 | Shroot et al. | 514/443 |
| 4,937,068 | 6/1990 | Baral | 424/63 |

OTHER PUBLICATIONS

"Amid growing demand for the skin-restoring drug Retin-A, dermatologist advise caution", personal Health Column, NY Times, Jun. 16, 1988, Jane Brody.
Drug Facts and Comparisons; 1990 Ed. Lippincott Co. pp. 2083-2085.
AHFS Drug Information; 1989 Ed. Am. Soc. Hosp. Pharmacist pp. 1988-1989.
Weiss, et al. "Topical Tietinoin Improves Photoaged Skin" JAMA, Jan. 22/29, 1988 vol. 259, No. 4 pp. 527-529 and 532.
"At last! A Medical Treatment for Skin Aging" editorial JAMA, Jan. 22/29, 1988 vol. 259, No. 4 pp. 569-570.

*Primary Examiner*—Paul R. Michl
*Assistant Examiner*—William E. Benston
*Attorney, Agent, or Firm*—David P. Gordon

[57] ABSTRACT

This invention relates generally to an improved medication and treatment serving to darken the color of some hair adjacent to the skin to which the materials of the treatment are applied. The treatment consists of application of topical tretinoin to the skin of a person combined with the application of a lotion containing ammonium lactate to the same skin area. When the treatment is continued on a basis of once or twice per day, the skin of the user assumes a uniform light brown color similar to the countenance of a suntanned appearance within a period of a few weeks, and some hair adjacent to the skin to which the materials of the treatment are applied is darkened.

16 Claims, No Drawings

COMPOSITION AND TREATMENT FOR DARKENING HAIR COLOR

This is a continuation of co-pending application Ser. No. 07/623,352 filed on Dec. 7, 1990, now abandoned.

FIELD OF THE INVENTION

This invention relates generally to an improved composition and treatment for darkening the color of gray hair of the user.

BACKGROUND OF THE INVENTION

There is a substantial desire shared by many people to have a "suntanned" appearance and to darken gray hair. Conventional methods include exposure to the sun and or to the rays of electrical lights in the case of skin tanning procedures. Such methods may be harmful and are time consuming.

STATEMENT OF PRIOR ART

The prior art is exemplified by the following patents, (U.S. except where otherwise noted) and papers in professional journals:

| | | | |
|---|---|---|---|
| 3,729,568 | 3,729,568 | 3,906,108 | 4,740,432 |
| 4,654,354 | 4,608,392 | 4,148,924 | 4,545,977 |
| 4,695,452 | 4,740,519 | 4,105,783 | 4,234,599 |

"Retin-A—The Real Scoop (Carla Rohfing) Self Magazine pp 174-179 May 1988

"At Last! A Medical Treatment for Skin Aging" Journal American Medical Association Jan. 22/29, 1988 Vol. 259 pp 569-570

"Topical Tretinoin Improves Photoaged Skin"—Weiss, Ellis, Headington et al—JAMA Jan. 22/29, 1988 Vol 59

"Personal Health"—Jane E. Brody—New York Times page B11 Thursday, Jun. 16, 1988

These references report on the improvement of photoaged or sun-damaged skin and the treatment of acne, skin keratoses or dry skin disorders, by the topical treatment of tretinoin to the skin of a person, but none suggest that a suntanned appearance or the darkening of gray hair can be produced by a treatment of a topical application of a tretinoin and lactate base lotion.

Such art is generally illustrative of various treatments and medicines in the field of the invention. While such medications are usually acceptable for their intended purposes, they do not meet the need of the user for a treatment of the skin to color the skin to provide a "suntanned" appearance or to darken the color of gray hair of a person. As a result of the shortcomings of the prior art, typified by the above, there has developed and continues to exist a substantial need for the product and treatment of the character described. Despite this need, and the efforts of many individuals and companies to develop such processes, a satisfactory product meeting this need has heretofore been unavailable.

The principal object of my invention is to provide a product of this character which combines simplicity, and reliability together with inexpensiveness of use. Other uses and advantages of the invention are completely and in part hereinafter pointed out.

SUMMARY OF THE INVENTION

This invention relates generally to an improved composition and treatment to induce a "suntanned" appearance by tanning the skin of the user without the need for harmful exposure to the rays of the sun or to the rays of electrical lights that produce infrared and/or ultra-violet light. This treatment may also serve to darken the color of some hair adjacent to the skin to which the materials of the treatment are applied. The treatment consists of application of topical tretinoin to the skin of the person combined with the application of a lotion containing ammonium lactate to the same skin area.

When the treatment is continued on a basis of once or twice per day, the skin of the user assumes a uniform light brown color similar to the countenance of a suntanned appearance within a period of a few weeks. A slight ruddiness, similar to the ruddy color previously reported with the application of tretinoin, may be also noticeable, but this ruddiness or redness is of a different cast than the uniform light brown color produced on the skin by the treatment of this invention.

I have also found that the treatment of my invention serves as an improved composition and treatment to darken the color of some gray hair growing out of skin areas to which the treatment has been applied.

DETAILED DESCRIPTION OF THE PREFERRED EMBODIMENT

My invention is a topical application of a combination of two sets of ingredients, either applied together in a common mixture, or applied independently as topical applications to the skin of a person for the purpose of producing a suntanned appearance in the skin of the user, and or causing the darkening of the color of some of the grayed hair growing out of skin areas to which the treatment has been applied.

The treatment consists of the topical application, on a regular basis over a period of time, of a salve containing tretinoin to the skin of a person combined with the application of a lotion containing a lactate salt such as ammonium lactate to the same skin area. When the treatment is continued on a basis of once or twice per day, the skin of the user assumes a uniform light brown color similar to the countenance of a suntanned appearance, within a period of less than several weeks.

A slight ruddiness, similar to the ruddy color previously reported with the application of tretinoin, may be also noticeable, but this ruddiness or redness is of a different cast than the uniform light brown color caused by the treatment of the invention.

I have found the topical application to the skin of a person of tretinoin in the form of a cream base or gel base in concentration ranging from 0.05% to 0.10% once or twice a day, with the topical application to the same skin area of a lotion of 12% concentration of ammonium lactate found in the lotion labeled with the trademark "LAC-HYDRIN" brand lotion manufactured by Westwood Pharmaceuticals Inc., on a basis of once or twice a day. This results in the development, within 3 weeks time, of a "suntanned" and youthful appearance to the surface of the person that has been so treated, and in circumstances where the treated person has not been subjected to normal sunlight exposure.

This tanned appearance also obscures the presence of wrinkles which are less visible after treatment has had its effect.

The suntanned appearance which is produced is quite different from the ruddy color that has been previously reported from the application of tretinoin to human skin, although this ruddiness may also be apparent.

My treatment produces a combination of a uniform light brown color, slight ruddiness, softened skin texture and decreased wrinkling, particularly when applied to facial surfaces of the person. Grayed hair growing from the area of skin that is treated may also become darkened in many cases.

In the case of a patient whose face showed severe acne scarring, a previous topical treatment of tretinoin had produced little or no effect over a six week period. When started on the described regimen of simultaneous topical treatment of both tretinoin gel sold under the trademark of "RETIN-A" (manufactured by Ortho Pharmaceutical Corporation) and ammonium lactate lotion sold under the trademark "LAC-HYDRIN", twice daily, her scarring became less visible and her facial skin developed a light brown color within a period of 30 days time.

In another case, the topical application of a 0.05% cream base lotion initially applied to the face, once a day, with the treatment subsequently changed to the topical application of 0.1% cream base lotion or 0.025% gel base lotion as found in "RETIN-A" trademark brand of lotion, applied twice a day did not produce any "suntanned" appearance to the face over a 10 day period. However, the subsequent continuance of that regime combined with the application of "LAC-HYDRIN" trademark brand of ammonium lactate 12% lotion, (manufactured by Westwood Pharmaceuticals Corp.) resulted in the development of a suntanned appearance that was noticeable to others. The topical treatment was continued over a six week period with the suntanned appearance of the face of the user becoming more noticeable and with a noticeable decrease in the visibility of wrinkles apparent to observers, after three weeks of treatment.

While I have used commercial preparations which are readily available to medical professional people, the source of active ingredients as well as the concentration of active ingredients may be varied together with appropriate change of cycle of topical application to obtain the same suntanned appearance on the skin of the patient or user. Although the treatment can be performed by the use of separate topical applications of a tretinoin-containing preparation and a lactate containing preparation, the two necessary ingredients may be combined in a lotion or lotion that may be topically applied by the user at the one time to produce the skin-tanning effect.

By combining the essential ingredients in the one preparation, it is possible to assure the user that he will be applying a uniform mixture of the ingredients at the optimum concentrations of each to the other.

It will be appreciated that persons who have unusual medical problems, and pregnant women are advised to consult a doctor prior to using this treatment.

It is thought that persons skilled in the art to which this invention relates will be able to obtain a clear understanding of the invention after considering the foregoing description in connection with the accompanying drawing. Therefore, a more lengthy description is deemed unnecessary. It is understood that various changes in shape, size, and arrangement of the elements of this invention as claimed may be resorted to in actual practice, if desired.

I claim:

1. A method for darkening the color of hair of a user, comprising:
   repeatedly applying to an area of the scalp of said user a compound containing tretinoin over a period of time; and
   repeatedly applying to the same area of the scalp of said user a compound containing ammonium lactate over substantially the same period of time.

2. A method according to claim 1, wherein:
   said compound containing tretinoin is in the form of a cream base lotion.

3. A method according to claim 1, wherein:
   said compound containing tretinoin is in the form of a gel base lotion.

4. A method according to claim 1, wherein:
   said compound containing tretinoin is in the form of a lotion, in which the concentration of tretinoin is in the general range of 0.025% to 0.1%.

5. A method according to claim 1, wherein:
   said compound containing tretinoin is applied substantially twice a day and said compound containing ammonium lactate is applied at substantially the same time as the application of the tretinoin.

6. A method for darkening the color of hair of a user, comprising:
   repeatedly applying a composition containing both a quantity of tretinoin and a quantity of lactate material to the scalp of said user over a period of time.

7. A method according to claim 6, wherein:
   said lactate material is ammonium lactate.

8. A method according to claim 1, wherein:
   said compound containing tretinoin is in the form of a lotion distributed under the trademark "RETIN-A".

9. A method according to claim 1, wherein:
   said compound containing ammonium lactate comprises a lotion in which the concentration of ammonium lactate is in the general range of 12%.

10. A method according to claim 1, wherein:
    said compound containing ammonium lactate is in the form of a preparation distributed under the trademark "LAC-HYDRIN".

11. A lotion for topical application to the scalp for darkening the color of the hair growing from the scalp, said lotion comprising:
    a composition for repeated applications over a period of time to the area of the scalp from which said hair that is to be darkened grows, said composition comprising a mixture of tretinoin and a lactate compound provided in sufficient concentrational amounts to enable said darkening of said hair, said composition also enabling the simultaneous topical application of both said tretinoin and said lactate compound in uniform proportions to said area of the scalp from which said hair that is to be darkened grows.

12. A lotion according to claim 11, wherein:
    said lactate compound is ammonium lactate, and
    said tretinoin is present in said lotion in the general range of 0.025% to 0.1% and said ammonium lactate is present in said lotion in the amount of about 12%.

13. A method according to claim 7, wherein:
    said composition is in the form of a cream base lotion.

14. A method according to claim 7, wherein:
    said composition is in the form of a gel base lotion.

15. A method according to claim 7, wherein:

said composition is in the form of a lotion in which the concentration of tretinoin is in the range of 0.0125% to 0.1%, and the concentration of ammonium lactate is in the range of 6% to 12%.

16. A lotion according to claim 11, wherein: said lactate compound is ammonium lactate, and said tretinoin is present in said lotion in the general range of 0.0125% to 0.1%, and said ammonium lactate is present in said lotion in the general range of 6% to 12%.

* * * * *